United States Patent [19]
Thielert et al.

[11] Patent Number: 6,040,271
[45] Date of Patent: Mar. 21, 2000

[54] SELECTIVE HERBICIDES FOR THE CULTIVATION OF SUGAR CANE

[75] Inventors: Wolfgang Thielert, Bury St. Edmunds, United Kingdom; Gerhard Bohne, Langenfeld; Klaus-Helmut Müller, Düsseldorf, both of Germany

[73] Assignee: Bayer Aktiengesellschaft, Leverkusen, Germany

[21] Appl. No.: 09/026,857

[22] Filed: Feb. 20, 1998

[51] Int. Cl.[7] .................. A01N 43/653; A01N 43/70; A01N 47/30
[52] U.S. Cl. ............................. 504/134; 504/139
[58] Field of Search ..................... 504/134, 139

[56] References Cited

U.S. PATENT DOCUMENTS 5,194,085  3/1993  Lindig et al. ........................ 504/273

OTHER PUBLICATIONS

The Agrochemicals Handbood, 3rd ed. "Ametryn", "Tebuthiuron", 1991.

Primary Examiner—S. Mark Clardy
Attorney, Agent, or Firm—Norris, McLaughlin & Marcus, P.A.

[57] ABSTRACT

The invention relates to the use of 4-amino-5-isopropyl-2-(tert-butyl-aminocarbonyl)-2,4-dihydro-3H-1,2,4-triazol-3-one alone, and also to synergistic active compound combinations for the cultivation of sugar cane which are characterized in that they contain an effective amount of an active compound combination comprising 4-amino-5-isopropyl-2-(tert-butylaminocarbonyl)-2,4-dihydro-3H-1,2,4-triazole-3-one and one or more compounds of a second group of herbicides consisting of the active compounds listed below:

ametryn,
tebuthiuron,
hexazinone,
isoxaflutole,
metribuzin,
sulfentrazone
diuron.

4 Claims, No Drawings

SELECTIVE HERBICIDES FOR THE CULTIVATION OF SUGAR CANE

The invention relates to the use of 4-amino-5-isopropyl-2-(tert-butyl-aminocarbonyl)-2,4-dihydro-3H-1,2,4-triazol-3-one alone in the cultivation of sugar cane and to synergistic active compound combinations which comprise 4-amino-5-isopropyl-2-(tert-butyl-aminocarbonyl)-2,4-dihydro-3H-1,2,4-triazol-3-one and known herbicidally active compounds on the other side and which can be employed particularly successfully for the selective control of weeds in sugar cane crops.

As broad-range herbicides, carbamoyltriazolinones are the subject of a number of patent applications (cf. EP-294 666, EP-370 293, EP-391 187, EP-398 096, EP-399 294, EP-415 196, EP-477 646). However, the known carbamoyltriazolinones have a number of activity gaps when used in sugar cane crops.

Surprisingly, it has now been found that 4-amino-5-isopropyl-2-(tert-butyl-aminocarbonyl)-2,4-dihydro-3H-1,2,4-triazol-3-one both alone and in the joint application with known herbicidally active compounds from various substance classes has pronounced synergistic effects in terms of herbicidal activity and can be used particularly advantageously as an active compound combination for the selective control of weeds in sugar cane crops.

This invention, accordingly, provides the use of 4-amino-5-isopropyl-2-(tert-butyl-aminocarbonyl)-2,4-dihydro-3H-1,2,4-triazol-3-one of the formula (A)

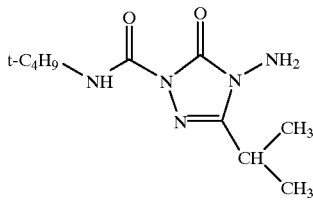

in the cultivation of sugar cane and synergistic selective herbicidal compositions based on this compound for the cultivation of sugar cane.

These compositions are characterized in that they contain an effective amount of an active compound combination comprising the active compound (A) and one or more compounds of a second group of herbicides which consist of the active compounds listed below:

N-ethyl-N'-(1-methylethyl)-6-(methylthio)-1,3,5-triazine-2,4-diamine (ametryn),

N-[5-(1,1-dimethylethyl)-1,3,4-thiadiazol-2-yl]-N,N'-dimethylurea (tebuthiuron), 3-cyclohexyl-6-(dimethylamino)-1-methyl-1,3,5-triazine-2,4(1H,3H)-dione (hexazinone), (5-cyclopropyl-isoxazol-4-yl)-(2-methylsulphonyl-4-trifluoromethylphenyl)-methanone (isoxaflutole, RPA-201 772), 4-amino-6-tert-butyl-3-methylthio-1,2,4-triazin-5(4H)-one (metribuzin), 2-(2,4-dichloro-5-methyl-sulphonylamino-phenyl)-4-difluoromethyl-5-methyl-2,4-dihydro-3H-1,2,4-triazol-3-one (sulfentrazone, F-6285), 3-(3,4-dichlorophenyl)-1,1-dimethylurea (diuron), ("active compound of Group 1").

Of particular interest are selective herbicidal compositions according to the invention which are characterized in that they contain an active compound combination comprising active compound (A) and one to three compounds from Group 1 of the abovementioned active compounds ametryn, tebuthiuron, hexazinone, isoxaflutole, metribuzin, sulfentrazone and diuron.

Of very particular interest are selective herbicidal compositions according to the invention which are characterized in that they contain an active compound combination comprising active compound (A) and one or two compounds from Group 1 of the abovementioned active compounds ametryn, tebuthiuron, hexazinone, isoxaflutole, metribuzin, sulfentrazone and diuron.

Surprisingly, it has now been found that both the active compound (A) alone and the above-defined active compound combinations of active compound (A) with the abovementioned active compounds of Group 1 have a particularly high herbicidal activity, while having good crop safety, and that they can be employed for the selective control of weeds in sugar cane crops.

Surprisingly, the selectivity in the sugar cane crops and the herbicidal activity of the active compound combinations according to the invention comprising active compound (A) and the compounds of Group 1 listed above is considerably higher than the sum of the activities of the individual active compounds.

This means that an unforeseeable synergistic effect in terms of herbicidal activity and not merely a complementation of action is present for the active compound combinations which, at the same time, display high selectivity in sugar cane. The novel active compound combinations are very well tolerated in sugar cane crops, and even weeds which are otherwise difficult to control are controlled well by the novel active compound combinations. The novel active compound combinations are therefore a useful addition to the range of the selective herbicides.

The active compound combinations according to the invention can be used for example in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Additionally, the active compounds according to the invention have excellent activity against weeds such as *Acanthospermum hispidum* DC., *Ageratum conycoides, Amaranthus chlorostachys, Brachiaria decumbens, Brachiaria plantaginea, Cenchrus echinatus* L., *Commelina benghalensis* L., *Desmodium tortuosum, Digitaria horizontalis, Digitaria sanguinalis, Eleusine indica, Euphorbia heterophylla* L., *Ipomoea* L. spec., *Ipomoea acuminata, Nicandra physaloides* (L.), *Panicum maximum, Portulaca oleracea* L., *Richardia brasiliensis, Rhynchelytrum repens, Sida rhombifolia* L., *Sonchus oleaceus* L., *Acanthospermum australe, Alternanthera tenella, Amaranthus viridis* L., *Arrhenatherum* P., *Bidens pilosa* L., *Cyperus rotundus* L., *Glycine max* (L.), *Sida cordifolia* L.

However, the use of the active compound combinations according to the invention is in no way restricted to these genera, but also extends in the same manner to other plants.

The synergistic effect of the active compound combinations according to the invention is especially pronounced at specific concentration ratios. However, the weight ratios of the active compounds in the active compound combinations can be varied within relatively wide ranges. In general, 0.001 to 1000 parts by weight, preferably 0.01 to 100 parts by weight, especially preferably 0.1 to 10 parts by weight, of active compound of Group 1 are used per part by weight of active compound (A).

The active compound combinations can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is possible to use other, for example organic solvents, as auxiliary solvents. Suitable liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Possible further additives are mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise a total of between 0.1 and 95% by weight, preferably between 0.5 and 90% by weight of active compound (A) alone or as an active compound combination together with one or more active compounds of the above-described Group 1.

The active compound (A) on its own, and also the active compound combinations according to the invention are preferably formulated individually and mixed upon application, that is to say applied in the form of tank mixes. However, they can also be applied in the form of ready mixes.

The active compound (A) on its own, and also the novel active compound combinations as such or in the form of their formulations can also be used as mixtures with further known herbicides, finished formulations or tank mixes again being possible. Mixtures with other known active compounds such as fungicides, insecticides, acaricides, nematicides, bird repellents, growth promoters, plant nutrients and soil conditioners, are also possible. Furthermore, it may be advantageous for specific purposes, in particular when using the post-emergence method, to incorporate mineral or vegetable oils tolerated by plants (for example "Oleo Dupont 11E", which is commercially available) or ammonium salts such as, for example, ammonium sulphate or ammonium thiocyanate, as further additives in the formulations.

The active compound (A) on its own, and also the novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound (A) on its own, and also the active compound combinations according to the invention can be applied before and after the emergence of the plants, i.e. by the pre-emergence and post-emergence method. They can also be incorporated into the soil prior to sowing.

The rates of application of the active compound (A) on its own, and also the active compound combinations according to the invention can be varied within a certain range; they depend, inter alia, on the weather and on the condition of the soil. In general, the rates of application are between 10 g and 10 kg per ha, preferably between 50 g and 5 kg per ha, in particular between 100 g and 2 kg per ha.

The good herbicidal activity of the active compound (A) on its own, and also of the novel active compound combinations is evident from the examples below. While the individual active compounds show weaknesses in their herbicidal activity, the combinations all exhibit very efficient control of weeds, and this control exceeds a simple sum of the activities.

In herbicides, a synergistic effect is always present when the herbicidal activity of the active compound combination exceeds that of the active compounds applied individually.

The expected activity for a given active compound combination of two herbicides can be calculated as follows (cf. COLBY, S. R.; "Calculating synergistic and antagonistic responses of herbicide combinations", Weeds 15, pages 20–22, 1967):

If $X = \%$ damage by herbicide A (active compound of the formula I) at the rate of application of p kg/ha and $Y = \%$ damage by herbicide B (active compound of the formula II) at the rate of application of q kg/ha and E=the expected damage caused by herbicides A and B at a rate of application of p and q kg/ha, then $E = X + Y - (X \cdot Y/100)$.

If the actual damage exceeds the calculated value, the combination is super-additive with regard to its activity, i.e. it shows a synergistic effect.

The examples below reveal that the herbicidal activity of the active compound combinations according to the invention found in the case of weeds exceeds the calculated value, i.e. that the novel active compound combinations have a synergistic action.

USE EXAMPLES

Example A

Pre-emergence test/outdoors

Solvent: 5 parts by weight of acetone

Emulsifier: 1 part by weight of alkylaryl polyglycol ether

To produce a suitable active compound preparation, 1 part by weight of active compound is in each case mixed with the stated amount of solvent, the stated amount of emulsifier is added and the concentrate is diluted with water to the desired concentration.

Shortly after the seeds of the test plants have been sown outdoors, the individual plots are watered with the amount of the active compound preparation required for wetting the soil evenly. The active compound concentration in the preparation does not matter, only the amount of active compounds applied per unit area is important.

After 5 weeks, the degree of damage to the test plants is scored visually in % damage in comparison with the development of the untreated control. The figures denote:

0%=no activity

100%=total destruction.

In this test, the active compound combination of (A) with ametryn and with tebuthiuron shows super-additive, i.e. synergistic activity against weeds typical in the cultivation of sugar cane.

Test result:

Mixture A: 0.56 kg/ha of active compound (A)+1.5 kg/ha of ametryn

Mixture B: 0.56 kg/ha of active compound (A)+0.75 kg/ha of tebuthiuron

Standard A: ametryn 2.5 kg/ha

Standard B: tebuthiuron 1 kg/ha

| Application method | Weed | Product/mixture | Efficacy |
|---|---|---|---|
| Pre-emergence | Euphorbia heterophylla | Mixture A | 97% |
| | | Mixture B | 97% |
| | | Standard A | 60% |
| | | Standard B | 30% |
| Pre-emergence | Sida rhombifolia | Mixture A | 100% |
| | | Mixture B | 100% |
| | | Standard A | 60% |
| | | Standard B | 40% |

We claim:

1. Herbicidal compositions comprising an active compound combination of 4-amino-5-isopropyl-2-(tert-butylaminocarbonyl)-2,4-dihydro-3H-1,2,4-triazol-3-one and one or more compounds selected from the group consisting of ametryn and diuron.

2. The herbicidal composition according to claim 1 for the cultivation of sugar cane, characterized in that they contain an effective amount of 4-amino-5-isopropyl-1-(tert-butyl-aminocarbonyl)-2,4-dihydro-3H-1,2,4-triazol-3-one and ametryn.

3. Process for preparing herbicidal compositions for the cultivation of sugar cane, characterized in that the herbicidal compositions according to claim 1 are mixed with extenders and/or surfactants.

4. A method for controlling undesirable plants in the cultivation of sugar cane, wherein 4-amino-5-isopropyl-2-(tert-butylaminocarbonyl)-2,4-dihydro-3H-1,2,4-triazol-3-one alone or in combination with one or more compounds selected from the group consisting of ametryn and diuron is allowed to act on undesirable plants and/or their habitat.

* * * * *